(12) United States Patent
Cheng et al.

(10) Patent No.: US 12,414,741 B2
(45) Date of Patent: Sep. 16, 2025

(54) PPG SIGNAL QUALITY EVALUATION METHOD AND APPARATUS AND PPG SIGNAL PROCESSING METHOD AND SYSTEM

(71) Applicant: Shenzhen Ninenovo Technology Limited, Shenzhen (CN)

(72) Inventors: Shijie Cheng, Shenzhen (CN); Qianjin Feng, Shenzhen (CN)

(73) Assignee: Shenzhen Ninenovo Technology Limited, Shenzhen (CN)

( * ) Notice: Subject to any disclaimer, the term of this patent is extended or adjusted under 35 U.S.C. 154(b) by 11 days.

(21) Appl. No.: 18/959,018

(22) Filed: Nov. 25, 2024

(65) Prior Publication Data

US 2025/0082276 A1    Mar. 13, 2025

Related U.S. Application Data

(63) Continuation of application No. PCT/CN2022/115490, filed on Aug. 29, 2022.

(30) Foreign Application Priority Data

May 27, 2022    (CN) .......................... 202210585033.1

(51) Int. Cl.
*A61B 5/00*    (2006.01)
*A61B 5/024*    (2006.01)

(52) U.S. Cl.
CPC ........ *A61B 5/7221* (2013.01); *A61B 5/02416* (2013.01); *A61B 5/7203* (2013.01); *A61B 5/7246* (2013.01); *A61B 5/725* (2013.01); *A61B 5/7257* (2013.01)

(58) Field of Classification Search
CPC . A61B 5/7221; A61B 5/02416; A61B 5/7203; A61B 5/7246; A61B 5/725; A61B 5/7257; A61B 5/02108; A61B 5/0261; A61B 5/7225; G06F 2218/04; G06F 2218/10; G06F 2218/14
See application file for complete search history.

(56) References Cited

FOREIGN PATENT DOCUMENTS

| CN | 103020472 A | 4/2013 |
|---|---|---|
| CN | 112494001 A | 3/2021 |
| CN | 112545472 A | 3/2021 |
| CN | 114528888 A | 5/2022 |

*Primary Examiner* — Serkan Akar
(74) *Attorney, Agent, or Firm* — George D. Morgan

(57) ABSTRACT

The present invention relates to a PPG signal quality evaluation method and apparatus and a PPG signal processing method and system. The PPG signal quality evaluation method includes: S1: acquiring an original signal; S2: when an average amplitude difference thereof is within a first preset range, executing S3, and otherwise, executing S11; S3: acquiring a useful signal; S4: when the high-frequency signal-to-noise ratio and the low-frequency signal-to-noise ratio thereof are respectively greater than corresponding first threshold values, executing S5, and otherwise, executing S11; S5: when the kurtosis and the skewness of a power spectrum of the useful signal are respectively greater than second threshold values, executing S6, and otherwise, executing S11; S6: when the average peak period of a correlation function is within a second preset range, executing S7, and otherwise, executing S11.

12 Claims, 12 Drawing Sheets

PPG SIGNAL QUALITY EVALUATION METHOD AND APPARATUS AND PPG SIGNAL PROCESSING METHOD AND SYSTEM

CROSS-REFERENCE TO RELATED APPLICATIONS

The application claims priority to Chinese patent application No. 202210585033.1, filed on May 27, 2022, the entire contents of which are incorporated herein by reference.

TECHNICAL FIELD

The present invention relates to the technical field of signal analysis and processing, and in particular, to a PPG signal quality evaluation method and apparatus and a PPG signal processing method and system.

BACKGROUND

Photoplethysmograph (PPG) technology is a technique for measuring changes in blood flow during an individual heartbeat cycle by using photoelectric methods. The PPG technology mainly uses a photodiode to emit to the skin, and then obtains waveforms capable of reflecting blood flow by receiving the intensity of reflected light. These waveforms contain rich physiological information of the human body. Due to its portability, low cost, and non-invasive nature, PPG is increasingly popular among technology companies and research institutions, and has been widely applied in heart rate detection, blood oxygen calculation, blood pressure estimation, and calculation of physiological indicators such as sleep staging.

However, PPG is inevitably interfered by power frequency noise, motion artifacts, and ambient light during an actual collecting process. When the PPG waveform is severely distorted or there is severe noise, it is impossible to obtain available PPG waveforms for accurate calculation of physiological indicators through preprocessing techniques such as filtering. Therefore, before calculating the physiological indicators, it is necessary to evaluate the quality of PPG signals, discard unavailable PPG signals that are severely distorted, and select high-quality and clean PPG signals for calculation of the physiological indicators. This can effectively improve the accuracy of calculation of the physiological indicators, reduce power consumption of wearable devices, and provide objective quantitative indicators for PPG signal quality evaluation when cooperating with hardware circuit selection and embedded parameter adjustment.

Currently available methods include a template matching method, a feature extraction-machine learning method, and a deep learning method. The template matching method mainly includes: splitting a section of PPG signal into individual heartbeat cycles, finding a representative heartbeat cycle template and then matching the same with all heartbeat cycles, and evaluating the one with a high matching ratio as a high-quality PPG waveform. However, such method relies greatly on a cycle splitting algorithm because the form of PPG waveforms is very complex and diverse, and inaccurate cycle splitting may mistakenly evaluate good signals as poor signals, and in addition, such method relies greatly on template selection criteria because inaccurate template selection may greatly affect the robustness of the algorithm. The machine learning and deep learning-based methods can also achieve good results, but they rely on accuracy of labels and generalization of datasets, and have a time-consuming process of labeling data. Moreover, evaluation results from most of the methods are only binary classifications of dividing the signals into available or available signals, resulting in rough classification results.

SUMMARY

The technical problem to be solved by the present invention is to provide a PPG signal quality evaluation method and apparatus and a PPG signal processing method and system.

A technical solution used by the present invention to resolve the technical problem is: providing a PPG signal quality evaluation method, including the following steps:

S1: acquiring an original PPG signal in a preset duration, where the PPG signal is a photoplethysmography signal;

S2: preprocessing the original PPG signal to obtain a plurality of waveform segments in preset lengths, acquiring average amplitude difference of the plurality of waveform segments, and determining whether the average amplitude difference is within a first preset range, when the average amplitude difference is within the first preset range, executing S3, and otherwise, executing S11;

S3: performing high-pass filtering and low-pass filtering on the original PPG signal respectively, and acquiring a useful signal of the original PPG signal on the basis of the results of the high-pass filtering and low-pass filtering;

S4: acquiring a high-frequency signal-to-noise ratio of the original PPG signal on the basis of the useful signal and the result of the high-pass filtering, acquiring a low-frequency signal-to-noise ratio of the original PPG signal on the basis of the useful signal and the result of the low-pass filtering, and determining whether the high-frequency signal-to-noise ratio and the low-frequency signal-to-noise ratio are respectively greater than corresponding first threshold values, when the high-frequency signal-to-noise ratio and the low-frequency signal-to-noise ratio are respectively greater than corresponding first threshold values, executing step S5, and otherwise, executing step S11;

S5: acquiring an autocorrelation function of the useful signal, performing Fourier transform on the autocorrelation function to obtain a power spectrum of the useful signal, acquiring kurtosis and skewness of the power spectrum respectively, and determining whether the kurtosis and the skewness of the power spectrum are respectively greater than corresponding second threshold values, when the kurtosis and the skewness of the power spectrum are respectively greater than corresponding second threshold values, executing step S6, and otherwise, executing step S11;

S6: acquiring an average peak period of the autocorrelation function, and determining whether the average peak period is within a second preset range, when the average peak period is within the second preset range, executing step S7, and otherwise, executing step S11;

S7: acquiring a maximum peak value and a standard deviation of a peak period of the autocorrelation function, and determining whether the maximum peak value is larger than a third threshold value or the standard deviation of the peak period is smaller than a fourth threshold value, when the maximum peak value is larger than the third threshold value or the standard deviation of the peak period is smaller than the fourth threshold value, executing step S8, and otherwise, executing step S11;

S8: acquiring a standard deviation of a peak-to-peak difference value of the autocorrelation function, and determining whether the standard deviation of the peak-to-peak difference value is smaller than a fifth threshold value, when the standard deviation of the peak-to-peak difference value is smaller than the fifth threshold value, executing step S9, and otherwise, executing step S10;

S9: determining the original PPG signal to be a first-grade signal, and ending;

S10: determining the original PPG signal to be a second-grade signal, where quality of the second-grade signal is lower than that of the first-grade signal, and ending; and S11: determining the original PPG signal to be a third-grade signal, where quality of the third-grade signal is lower than that of the second-grade signal, and ending.

Preferably, in the PPG signal quality evaluation method according to the present invention, in the step S1, the preset duration is greater than or equal to 5 s and less than or equal to 15 s.

Preferably, in the PPG signal quality evaluation method according to the present invention, in the step S2, the preprocessing the original PPG signal to obtain a plurality of waveform segments in preset lengths includes:

performing median filtering on the original PPG signal, and sequentially performing non-interval interception on a filtered signal using a sliding window of the preset length to obtain the plurality of waveform segments, where the waveform segments do not overlap; and/or, the acquiring average amplitude difference of the plurality of waveform segments includes:

acquiring amplitude difference of each waveform segment, and acquiring an average value of amplitude difference of all the waveform segments as the average amplitude difference.

Preferably, in the PPG signal quality evaluation method according to the present invention, the first preset range is greater than or equal to 150 and less than or equal to 90000; and/or, the preset length is 1 s.

Preferably, in the PPG signal quality evaluation method according to the present invention, in the step S3, the performing high-pass filtering and low-pass filtering on the original PPG signal respectively, and acquiring a useful signal of the original PPG signal on the basis of the results of the high-pass filtering and low-pass filtering includes:

S31: performing high-pass filtering on the original PPG signal through a Butterworth high-pass filter with a cutoff frequency as a first frequency to obtain a high-frequency noise signal;

S32: performing low-pass filtering on the original PPG signal through a Butterworth high-pass filter with a cutoff frequency as a second frequency to obtain a low-frequency noise signal; and S33: eliminating the high-frequency noise signal and the low-frequency noise signal from the original PPG signal respectively, and using a residual signal as the useful signal.

Preferably, in the PPG signal quality evaluation method according to the present invention, in the step S4, the acquiring a high-frequency signal-to-noise ratio of the original PPG signal on the basis of the useful signal and the result of the high-pass filtering includes: acquiring a ratio of the high-frequency noise signal to the useful signal as the high-frequency signal-to-noise ratio; and the acquiring a low-frequency signal-to-noise ratio of the original PPG signal on the basis of the useful signal and the result of the low-pass filtering includes: acquiring a ratio of the low-frequency noise signal to the useful signal as the low-frequency signal-to-noise ratio.

Preferably, in the PPG signal quality evaluation method according to the present invention, in the step S4, a first threshold value corresponding to the high-frequency signal-to-noise ratio is larger than or equal to 6 dB, and the first threshold value corresponding to the low-frequency signal-to-noise ratio is larger than or equal to −15 dB; and/or, in the step S5, a second threshold value corresponding to the skewness of the power spectrum is larger than or equal to 12, and a second threshold value corresponding to the kurtosis of the power spectrum is larger than or equal to 150.

Preferably, in the PPG signal quality evaluation method according to the present invention, in the step S5, the acquiring an autocorrelation function of the useful signal includes: performing a unilateral normalization autocorrelation function on the useful signal, where the autocorrelation function meets the following formula:

$$R[k] = \frac{\sum_{n=0}^{N-1-k} x_s[n] x_s[n+k]}{\sum_{n=0}^{N-1} (x_s[n])^2}, k = 0, 1, \ldots, N-1$$

where R[k] is the autocorrelation function, k is an index value of the autocorrelation function, $x_s[n]$ is the useful signal, n is an index value of the useful signal, and N is the number of points of the useful signal.

Preferably, in the PPG signal quality evaluation method according to the present invention, the method further includes:

performing peak detection on the autocorrelation function by using a valley detection algorithm based on the second derivative to obtain a plurality of peak coordinates; and respectively acquiring an average peak period, a maximum peak value, a standard deviation of the peak period and a standard deviation of a peak-to-peak difference value of the autocorrelation function on the basis of the plurality of peak coordinates.

Preferably, in the PPG signal quality evaluation method according to the present invention, the method further includes one or more of the following parameter settings:

the second preset range is greater than 0.3 s and less than 2 s;

the third threshold value is larger than or equal to 0.6;

the fourth threshold value is smaller than or equal to 5; and the fifth threshold value is smaller than or equal to 0.07.

In addition, the present invention further provides a PPG signal processing method, including: acquiring a quality evaluation result of an original PPG signal through the PPG signal quality evaluation method according to any one of the above; and when the original PPG signal is a third-grade signal, eliminating the original PPG signal;

when the original PPG signal is a second-grade signal, using the original PPG signal to calculate partial preset physiological indicators; and when the original PPG signal is a first-grade signal, using the original PPG signal to calculate all physiological indicators related to the PPG signal.

In addition, the present invention further provides a PPG signal quality evaluation apparatus, including:

an original signal acquisition unit, configured to acquire an original PPG signal in a preset duration, where the PPG signal is a photoplethysmography signal;

a first determining unit, configured to preprocess the original PPG signal to obtain a plurality of waveform segments in preset lengths, acquire average amplitude difference of the plurality of waveform segments, and determine whether the average amplitude difference is within a first preset range, when the average amplitude difference is within the first preset range, output a positive result, and otherwise, output a negative result;

a useful signal acquisition unit, configured to perform high-pass filtering and low-pass filtering on the original PPG signal respectively, and acquire a useful signal of the original PPG signal on the basis of the results of the high-pass filtering and low-pass filtering;

a second determining unit, configured to acquire a high-frequency signal-to-noise ratio of the original PPG signal on the basis of the useful signal and the result of the high-pass filtering, acquire a low-frequency signal-to-noise ratio of the original PPG signal on the basis of the useful signal and the result of the low-pass filtering, and determine whether the high-frequency signal-to-noise ratio and the low-frequency signal-to-noise ratio are respectively greater than corresponding first threshold values, when the high-frequency signal-to-noise ratio and the low-frequency signal-to-noise ratio are respectively greater than corresponding first threshold values, output a positive result, and otherwise, output a negative result;

a third determining unit, configured to acquire an autocorrelation function of the useful signal, perform Fourier transform on the autocorrelation function to obtain a power spectrum of the useful signal, acquire kurtosis and skewness of the power spectrum respectively, and determine whether the kurtosis and the skewness of the power spectrum are respectively greater than corresponding second threshold values, when the kurtosis and the skewness of the power spectrum are respectively greater than corresponding second threshold values, output a positive result, and otherwise, output a negative result;

a fourth determining unit, configured to acquire an average peak period of the autocorrelation function, and determine whether the average peak period is within a second preset range, when the average peak period is within the second preset range, output a positive result, and otherwise, output a negative result;

a fifth determining unit, configured to acquire a maximum peak value and a standard deviation of a peak period of the autocorrelation function, and determine whether the maximum peak value is larger than a third threshold value or the standard deviation of the peak period is smaller than a fourth threshold value, when the maximum peak value is larger than the third threshold value or the standard deviation of the peak period is smaller than the fourth threshold value, output a positive result, and otherwise, output a negative result;

a sixth determining unit, configured to acquire a standard deviation of a peak-to-peak difference value of the autocorrelation function, and determine whether the standard deviation of the peak-to-peak difference value is smaller than a fifth threshold value, when the standard deviation of the peak-to-peak difference value is smaller than the fifth threshold value, output a positive result, and otherwise, output a negative result; and a result confirmation unit, configured to determine that the original PPG signal is a third-grade signal when any one of the first determining unit, the second determining unit, the third determining unit, the fourth determining unit, the fifth determining unit, and the sixth determining unit outputs a negative result, determine that the original PPG signal is a second-grade signal when the sixth determining unit outputs a negative result, and determine that the original PPG signal is a first-grade signal when the sixth determining unit outputs a positive result, where quality of the third-grade signal is lower than that of the second-grade signal, and quality of the second-grade signal is lower than that of the first-grade signal.

In addition, the present invention further provides a PPG signal processing system, including the PPG signal quality evaluation apparatus according to the above and a processing unit, where the processing unit is configured to acquire a quality evaluation result of an original PPG signal; and when the original PPG signal is a third-grade signal, eliminate the original PPG signal;

when the original PPG signal is a second-grade signal, use the original PPG signal to calculate partial preset physiological indicators; and when the original PPG signal is a first-grade signal, use the original PPG signal to calculate all physiological indicators related to the PPG signal.

According to the present invention, the PPG signal quality evaluation method and apparatus and a PPG signal processing method and system have the following beneficial effects: an evaluation of multi-level quantitative indicators of the PPG signal can be realized, so that reasonable utilization of different quality grades on the basis of the PPG signal is realized.

BRIEF DESCRIPTION OF THE DRAWINGS

The present invention is further described below with reference to the accompanying drawings and embodiments, in the accompanying drawings.

DETAILED DESCRIPTION OF THE EMBODIMENTS

In order to understand the technical features, objectives and effects of the present invention more clearly, embodiments of the present invention are described in detail with reference to the accompanying drawings.

Figure 1:
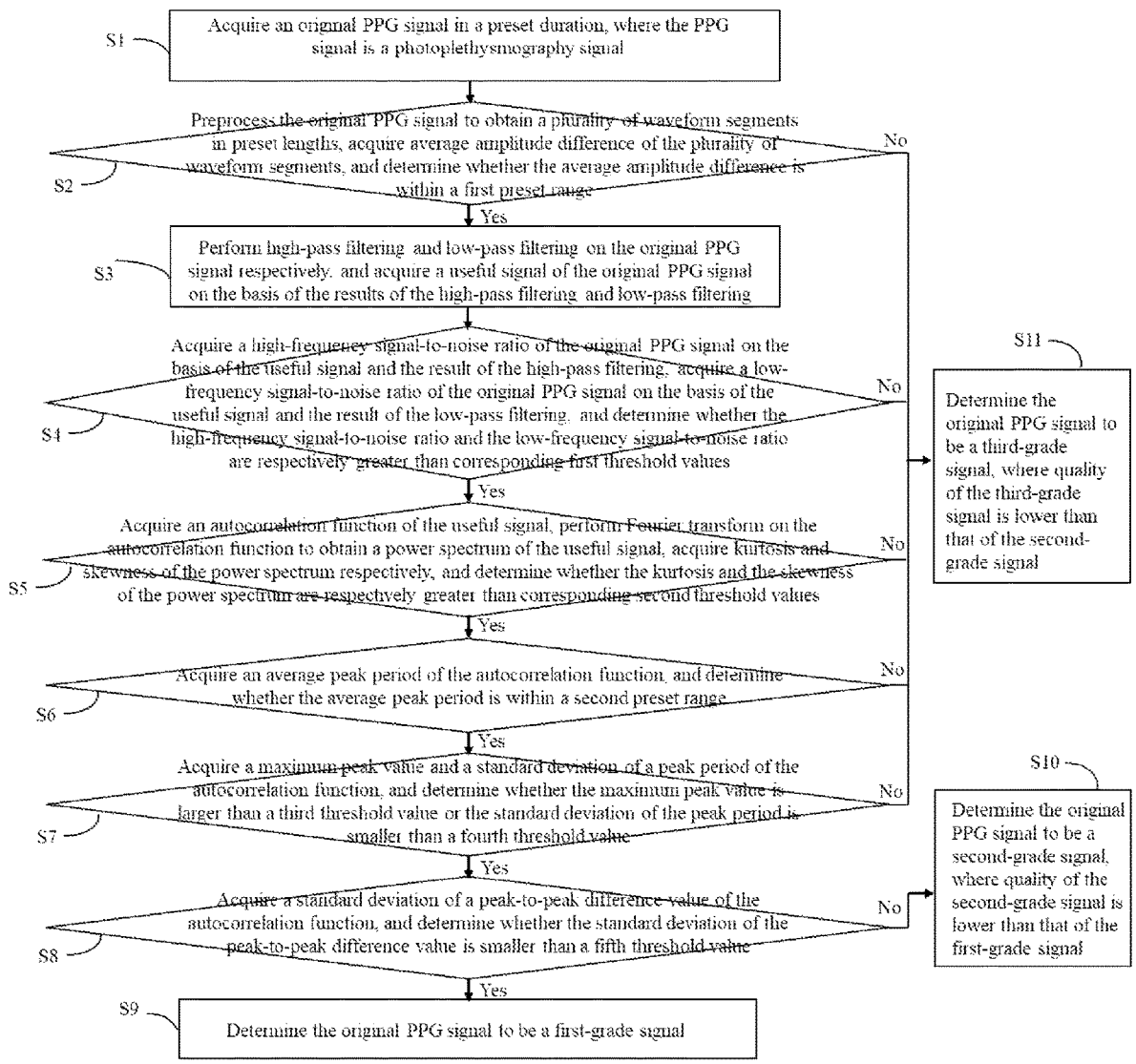
FIG. 1 is a program flowchart of a PPG signal quality evaluation method according to an embodiment of the present invention.
Figure 2:
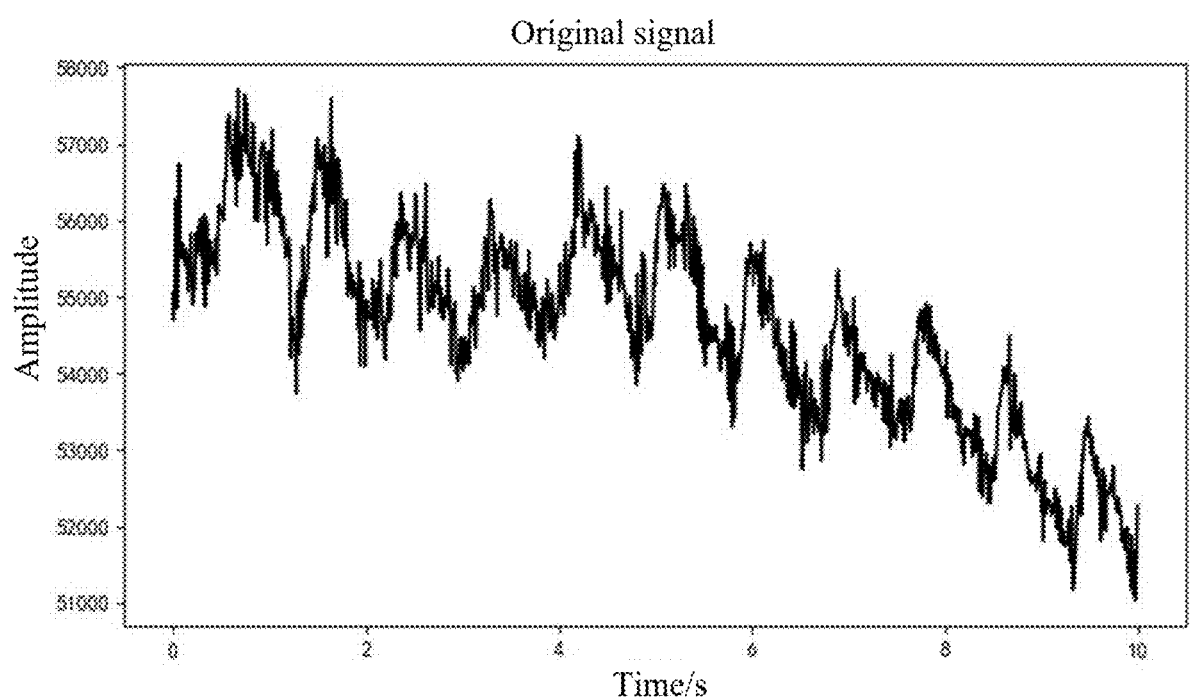
FIG. 2 is a schematic diagram of an original PPG signal according to an embodiment of the present invention.

As shown in FIG. 1, in a first embodiment of a PPG signal quality evaluation method of the present invention, the method includes the following steps: S1: acquire an original PPG signal in a preset duration, where the PPG signal is a photoplethysmography signal. Specifically, PPG information of a preset duration can be acquired through a collecting device, that is, corresponding to the original PPG signal. The duration of the original PPG signal cannot be set to be too long, otherwise, fluctuation of the signal is very violent, and calculation complexity is increased along with the increase of the duration. The duration of the original PPG signal is at least 5 s, and at most no more than 15 s. According to the normal minimum heart rate of 30 times per minute, a waveform of the 5 s time period contains at least two to three pulse periods. As shown in FIG. 2, the duration of the original PPG signal can be selected as 10 s, and when the original PPG signal corresponds to a sampling frequency $f_s=100$ Hz, the total number of points of the signals is 1000.

Figure 3:
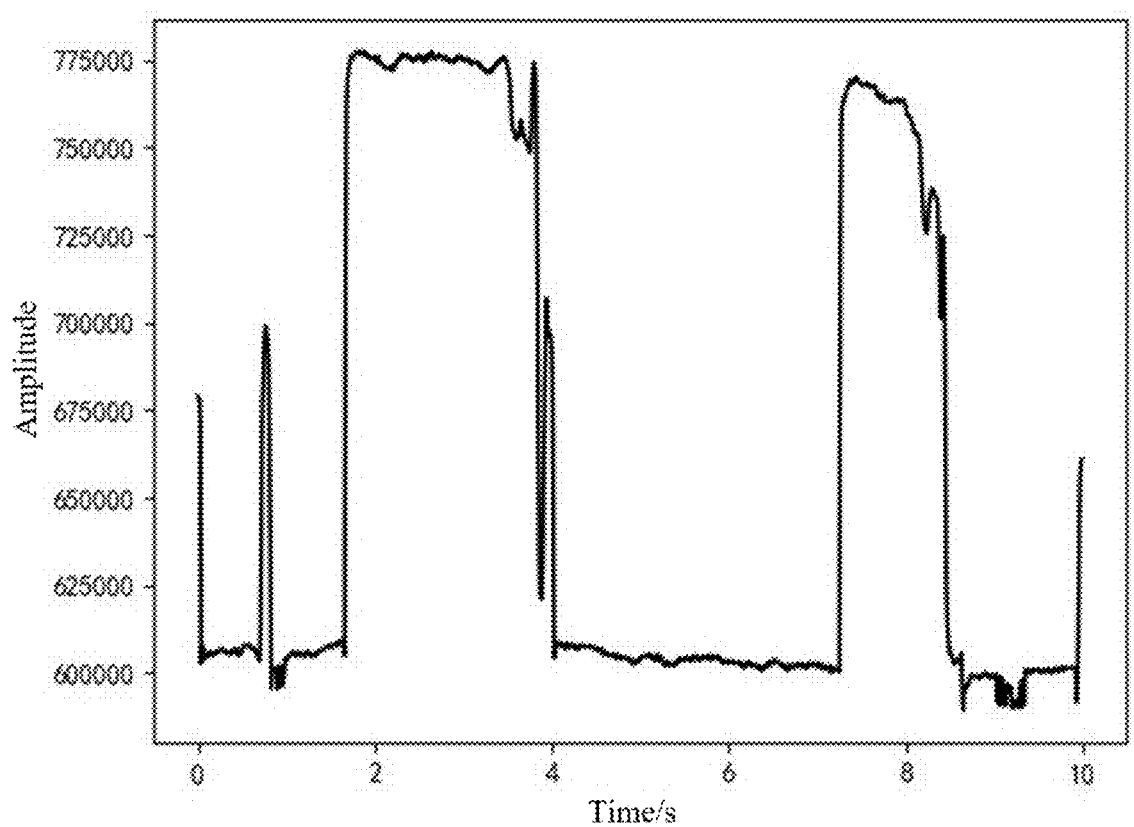
FIG. 3 is a schematic diagram of average amplitude difference of an original PPG signal according to an embodiment of the present invention.

S2: Preprocess the original PPG signal to obtain a plurality of waveform segments in preset lengths, acquire average amplitude difference of the plurality of waveform segments, and determine whether the average amplitude difference is within a first preset range, when the average amplitude difference is within the first preset range, execute S3, and otherwise, execute S11. Specifically, when the device is in poor contact with the skin or when the device is not worn, the original PPG signal obtained by the collecting device may be very weak or even not, and in this case, the average amplitude difference of the original PPG signal is very low. On the contrary, when saturation noise or a spike pulse occurs in a hardware circuit, the average amplitude difference of the signals become abnormally high. Therefore, the original PPG signal can be segmented to obtain the plurality of waveform segments in preset lengths, and the average amplitude difference of the waveform segments is obtained on the basis of the plurality of waveform segments. The average amplitude difference is determined. When the average amplitude difference meets the requirement of the first preset range, that is, in this case, it can be determined that the amplitude of the original PPG signal is normal, and the step S3 and the subsequent action can continue to be executed. When the average amplitude difference does not meet the requirement of the first preset range, it is determined that the amplitude of the original PPG signal is abnormal, and in this case, the subsequent determining action can be executed directly. That is, the original PPG signal can be directly determined to be a third-grade signal, and the quality evaluation process of the original PPG signal can be ended. The process can be defined as a first-level evaluation process, and the range of the average amplitude difference of a normal PPG waveform is hundreds to tens of thousands. However, when the device is in poor contact with the skin or when the device is not worn, and when the average amplitude difference of the PPG signal is lower than 150, the waveform of the PPG signal is approximately one straight line. As shown in FIG. 3, when a current in the hardware circuit is adjusted excessively, average amplitude difference of the PPG signal may be greater than 90000, and the waveform of the PPG signal may be saturated and distorted. If the average amplitude difference of the original PPG signal is abnormal, the original PPG signal is evaluated as a poor signal, and the next level of evaluation does not need to be performed. The 150 and 9000 here correspond to the numbers of signals after discretization, which are determined by the set quantization precision.

In an embodiment, in the above step S2, the preprocessing the original PPG signal to obtain a plurality of waveform segments in preset lengths includes: performing median filtering on the original PPG signal, and sequentially performing non-interval interception on a filtered signal using a sliding window of the preset length to obtain the plurality of waveform segments, where the waveform segments do not overlap. That is, median filtering with a window size of 5 can be performed on the original PPG signal first, and the influence of an outlier in the original PPG signal is eliminated to obtain a signal x[n]. In the filtering process of the median filtering, the median of the five numbers is taken, so that the influence of the abnormal outlier can be eliminated. For example, the signal is [1, 2, 3, 4, 25], and finally, 3 is output, so that the influence of the outlier 25 is avoided. The signal x[n] is divided into M non-overlapping segments by using a sliding window with an L-point length (corresponding to the preset length), and each segment is marked as:

$$x_m[l], 0 \le m \le M-1, 0 \le l \le L-1.$$

$x_m[l]$ is a waveform segment, a subscript m is an index value of the waveform segment, that is, representing the which small signal segment, and l is the length of the waveform segment. For example, for the signal x[n], a value of n is [0, N−1], which corresponds to signals of 10 s respectively. A waveform segment obtained when M is 10, a value of m is [0, M−1], which corresponds to signal segments of 1 s respectively.

In an embodiment, when the sampling frequency of the signal is set as $f_s=100$ Hz, the length of the signal x[n] is 10 s, and L is taken as 100 points, that is, the corresponding preset length can also be understood as s, and M=10.

In an embodiment, in the above step S2, the acquiring average amplitude difference of the plurality of waveform segments includes: acquiring amplitude difference of each waveform segment, and acquiring an average value of amplitude difference of all the waveform segments as the average amplitude difference. That is, the amplitude difference $\Delta_m$ of each waveform segment is calculated for the obtained waveform segment.

$$\Delta_m = \max(x_m[l]) - \min(x_m[l]).$$

$\max(x_m[l])$ is the maximum amplitude value in the $x_m[l]$ waveform segment, $\min(x_m[l])$ is the minimum amplitude value in the $x_m[l]$ waveform segment, and therefore, the average amplitude difference Amp of all waveform segments is obtained as follows:

$$Amp = \frac{1}{M}\sum_{m=0}^{M-1}\Delta_m.$$

The average amplitude difference Amp can be determined to meet the first preset range when the Amp is greater than or equal to 150 and less than or equal to 90000.

S3: Perform high-pass filtering and low-pass filtering on the original PPG signal respectively, and acquire a useful signal of the original PPG signal on the basis of the results of the high-pass filtering and low-pass filtering. Specifically, when the amplitude indicator of the original PPG signal meets the requirement, the noise of the original PPG signal continues to be determined. Although the main frequency of the PPG signal is 0.5 Hz-5 Hz, and a frequency that is greater than 5 Hz is a high-frequency burr noise of the signal, and the energy proportion is small; a frequency that is less than 0.5 Hz is a low-frequency noise related to baseline drift, accounting for most of energy. However, in the signal processing process, the influence of the high-frequency noise and the low-frequency noise needs to be determined respectively. It is assumed that a segment of signal has no baseline drift, that is, a low-frequency noise thereof is very small, but a high-frequency noise thereof is very large, then the segment of signal cannot be used due to too large high-frequency noise. Therefore, the high-frequency noise and the low-frequency noise in the segment of signal need to be eliminated, a useful signal of the original PPG signal is finally obtained, and the original PPG signal is determined on the basis of the useful signal.

Optionally, in the step S3, the performing high-pass filtering and low-pass filtering on the original PPG signal respectively, and acquire a useful signal of the original PPG signal on the basis of the results of the high-pass filtering and low-pass filtering includes: S31: performing high-pass filtering on the original PPG signal through a Butterworth high-pass filter with a cutoff frequency as a first frequency to obtain a high-frequency noise signal; S32: performing low-pass filtering on the original PPG signal through a Butterworth high-pass filter with a cutoff frequency as a second frequency to obtain a low-frequency noise signal; and S33: eliminating the high-frequency noise signal and the low-frequency noise signal from the original PPG signal respectively, and using a residual signal as the useful signal. Specifically, the original PPG signal may be separately filtered through the high-pass filter to obtain the high-frequency noise signal and filtered through the low-pass filter to obtain the low-frequency noise signal. The Butterworth filter can be adopted for both the high-pass filter and the low-pass filter. In addition, the cutoff frequency, that is, the first frequency of the high-pass filter can be set as $f_{high}$=5 H$_z$, so as to obtain the high-frequency noise signal $X_{high}[n]$, and then the high-frequency noise power $P_{high}$ is as follows:

$$P_{high} = \frac{1}{N}\sum_{n=0}^{N-1}|x_{high}[n]|^2.$$

The cutoff frequency, that is, the second frequency of the low-pass filter can be set as $f_{low}$=0.5 H$_z$, so as to obtain the low-frequency noise signal $X_{low}[n]$, and then the low-frequency noise power $P_{low}$ is as follows:

$$P_{low} = \frac{1}{N}\sum_{n=0}^{N-1}|x_{low}[n]|^2.$$

Finally, the high-frequency noise signal and low-frequency noise signal are subtracted from the original PPG signal respectively to obtain the corresponding useful signal $X_s[n]$, and then the useful signal power $P_s$ is as follows:

$$P_s = \frac{1}{N}\sum_{n=0}^{N-1}|x_s[n]|^2.$$

It can be understood that after the signal is filtered, the length corresponding to the high-frequency noise signal $X_{high}[n]$ and the low-frequency noise signal $X_{low}[n]$ is the same as the length of the original signal x[n], for example, N=1000.

Figure 4:
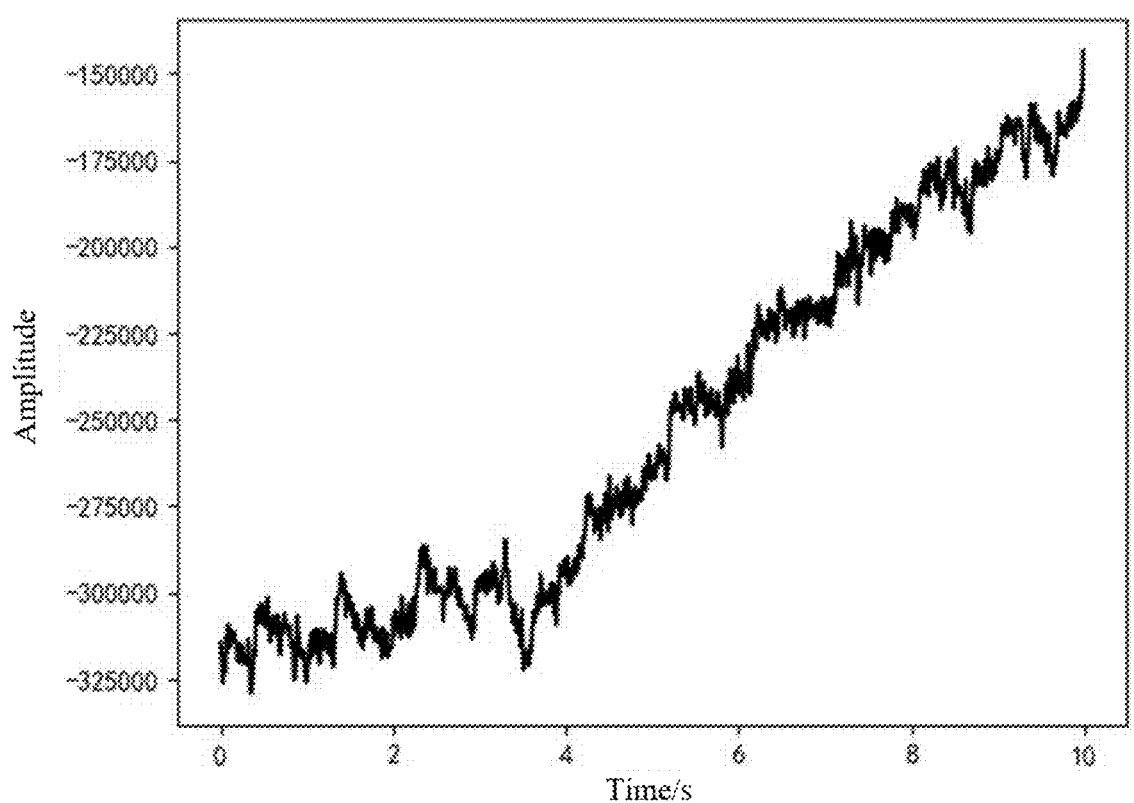
FIG. 4 is a schematic diagram of a low-frequency signal-to-noise ratio of an original PPG signal according to an embodiment of the present invention.
Figure 5:
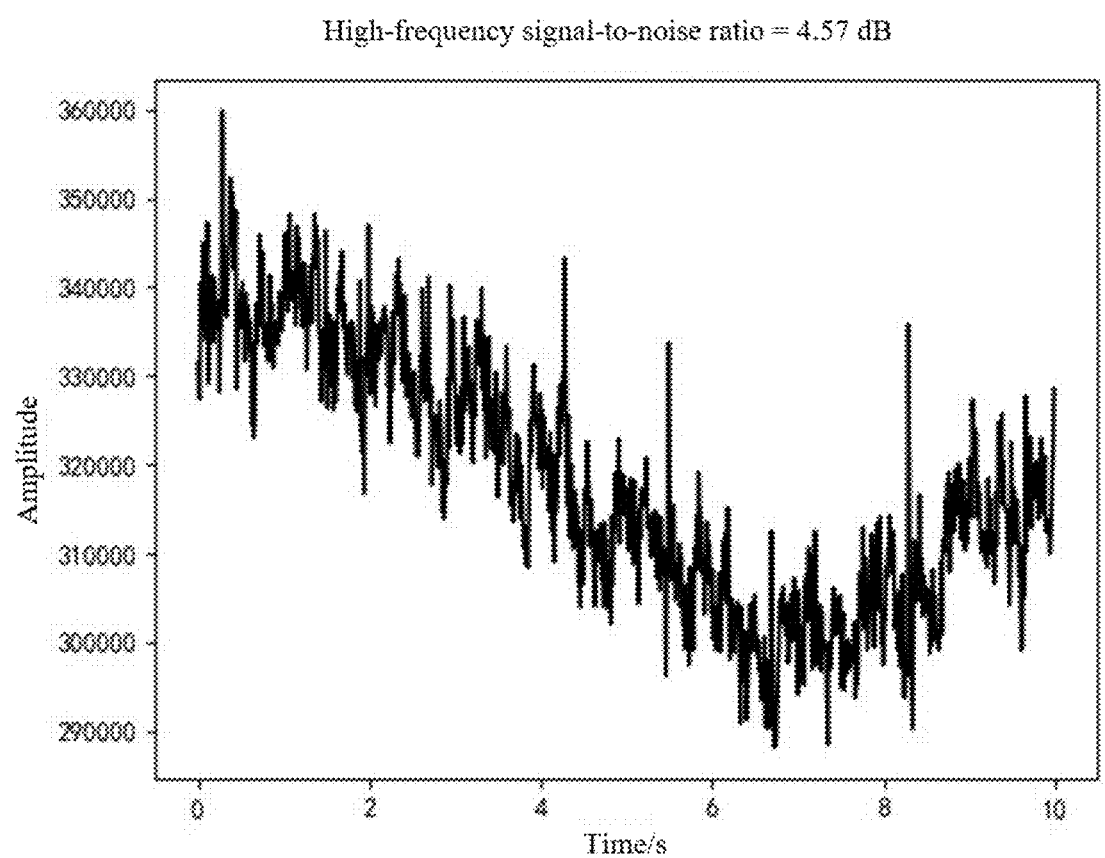
FIG. 5 is a schematic diagram of a low-frequency signal-to-noise ratio of an original PPG signal according to an embodiment of the present invention.

S4: Acquire a high-frequency signal-to-noise ratio of the original PPG signal on the basis of the useful signal and the result of the high-pass filtering, acquire a low-frequency signal-to-noise ratio of the original PPG signal on the basis of the useful signal and the result of the low-pass filtering, and determine whether the high-frequency signal-to-noise ratio and the low-frequency signal-to-noise ratio are respectively greater than corresponding first threshold values, when the high-frequency signal-to-noise ratio and the low-frequency signal-to-noise ratio are respectively greater than corresponding first threshold values, execute step S5, and otherwise, execute step S11. Specifically, because effects of the high-frequency noise and the low-frequency noise on the original PPG signal are different, the high-frequency signal-to-noise ratio and the low-frequency signal-to-noise ratio need to be distinguished. The high-frequency signal-to-noise ratio and the low-frequency signal-to-noise ratio of the original PPG signal can be respectively obtained on the basis of the results of high-pass filtering and the low-pass filtering, and under the condition that the high-frequency signal-to-noise ratio and the low-frequency signal-to-noise ratio of the original PPG signal both meet the requirement, it is determined that the noise of the original PPG signal meets the requirement, and the subsequent action of the step S5 can continue to be executed. When any one of the high-frequency noise ratios and the low-frequency noise ratio does not meet the requirement, it can be determined that the noise of the original PPG signal is abnormal, and in this case, the subsequent determining action can be executed directly. That is, the original PPG signal can be directly determined to be a third-grade signal, and the quality evaluation process of the original PPG signal can be ended. The process can be defined as a second-level evaluation process. The noise of the PPG signal is mainly derived from high-frequency burr noise and low-frequency drift noise. As shown in FIG. 4, when the low-frequency signal-to-noise ratio is smaller than −15 dB, the overall drift of the PPG signal is very serious, the fluctuation is very violent, and the PPG signal is completely in an irregular state. As shown in FIG. 5, when the high-frequency signal-to-noise ratio is smaller than 6 dB, the form of the PPG waveform is completely covered by the burr, and the form and period of the PPG waveform cannot be observed even if the high-frequency noise signal and the low-frequency noise signal are eliminated. In conclusion, when the low-frequency signal-to-noise ratio is too low, the signal is very weak and covered by the noise, even energy of noise in a pass band is far higher than that of the signal, or the PPG signal is not detected at all. Therefore, when the signal-to-noise ratio is abnormal, the original PPG signal can be directly determined to be a poor signal, and a third-level evaluation does not need to be performed.

Optionally, in the step S4, the acquiring a high-frequency signal-to-noise ratio of the original PPG signal on the basis of the useful signal and the result of the high-pass filtering includes: acquiring the ratio of the high-frequency noise signal to the useful signal as the high-frequency signal-to-noise ratio; and the acquiring a low-frequency signal-to-noise ratio of the original PPG signal on the basis of the useful signal and the result of the low-pass filtering includes: acquiring the ratio of the low-frequency noise signal to the useful signal as the low-frequency signal-to-noise ratio. A specific process of acquiring the high-frequency signal-to-noise ratio $SNR_{high}$ is as follows:

$$SNR_{high} = 10 \times \log_{10} \frac{P_s}{P_{high}}.$$

A specific process of acquiring the low-frequency signal-to-noise ratio $SNR_{low}$ is as follows:

$$SNR_{low} = 10 \times \log_{10} \frac{P_s}{P_{low}}.$$

In an embodiment, a first threshold value corresponding to the high-frequency signal-to-noise ratio is larger than or equal to 6 dB, and the first threshold value corresponding to the low-frequency signal-to-noise ratio is larger than or equal to −15 dB. That is to say, when the first threshold value corresponding to the high-frequency signal-to-noise ratio is 6 dB, that is, when the high-frequency signal-to-noise ratio $SNR_{high}$ is larger than 6 dB, it can be determined that the high-frequency signal-to-noise ratio meets the requirement. When the first threshold value corresponding to the low-frequency signal-to-noise ratio is 15 dB, that is, when the low-frequency signal-to-noise ratio $SNR_{low}$ is larger than 15 dB, it can be determined that the low-frequency signal-to-noise ratio meets the requirement.

Figure 6:
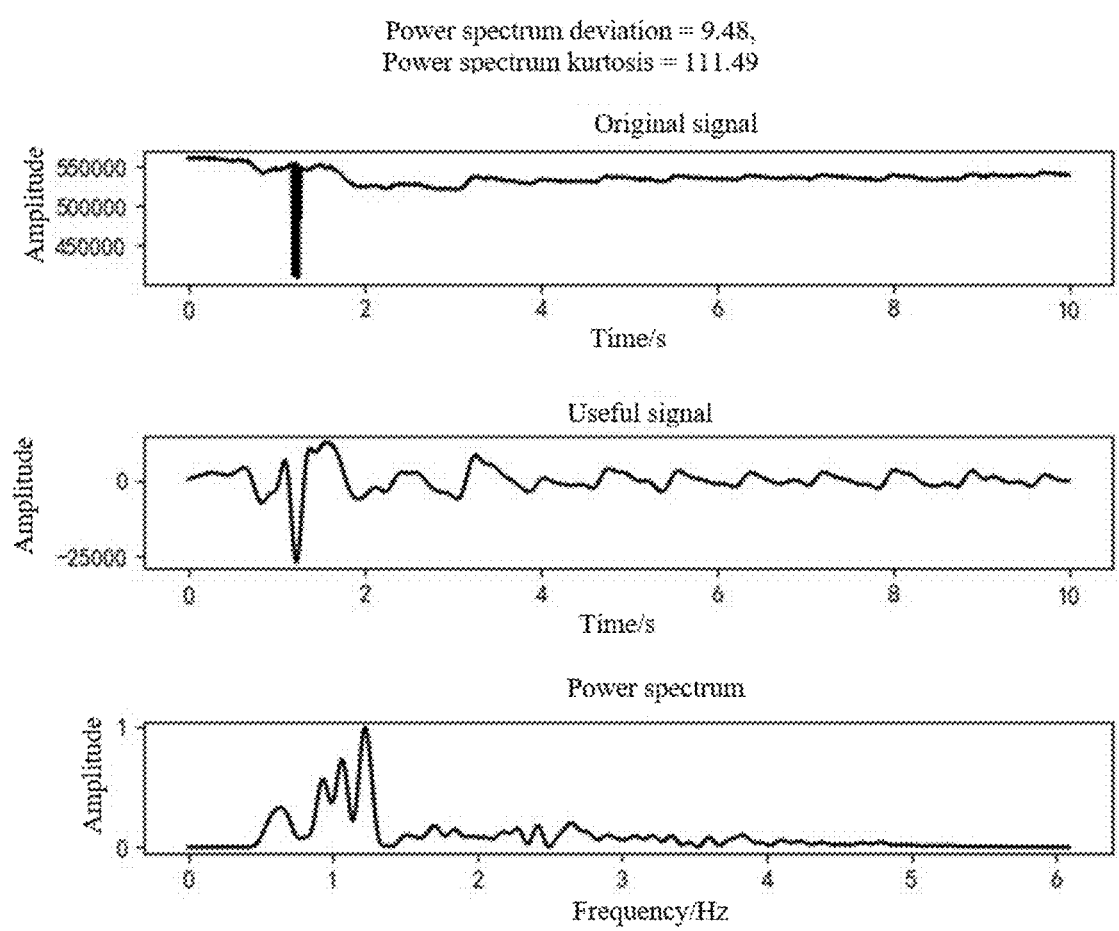
FIG. 6 is a schematic diagram of a power spectrum indicator of an original PPG signal according to an embodiment of the present invention.
Figure 7:
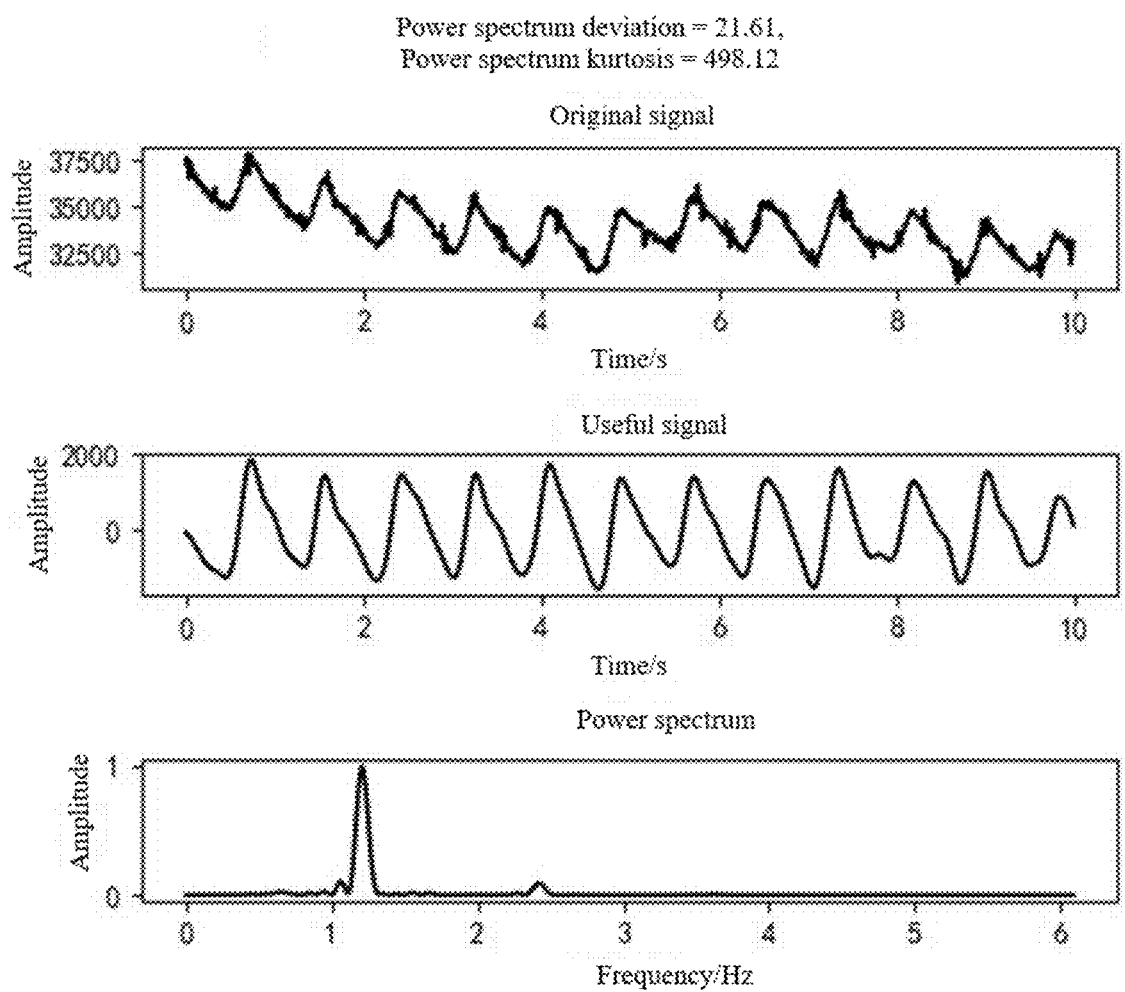
FIG. 7 is a schematic diagram of a power spectrum indicator of an original PPG signal according to another embodiment of the present invention.

S5: Acquire an autocorrelation function of the useful signal, performing Fourier transform on the autocorrelation function to obtain a power spectrum of the useful signal, acquire kurtosis and skewness of the power spectrum respectively, and determine whether the kurtosis and the skewness of the power spectrum are respectively greater than corresponding second threshold values, when the kurtosis and the skewness of the power spectrum are respectively greater than corresponding second threshold values, execute step S6, and otherwise, execute step S11. Specifically, when a noise indicator of the original PPG signal meets the requirement, an indicator related to the power spectrum is determined. Skewness and Kurtosis of a frequency spectrum corresponding to the original PPG signal are mainly determined. When discontinuous points and spike pulses exist in the original PPG signal, these sudden changes cause the power spectrum coefficients to be distributed on the whole frequency axis, and a good sparse representation cannot be obtained. The high-frequency signal-to-noise ratio and the low-frequency signal-to-noise ratio of such a sudden change signal can be very high and cannot be detected through an indicator related to the signal-to-noise ratio, but the sparse representation of the sudden change signal can be measured by calculating the skewness and the kurtosis of the power spectrum of the useful signal. First, the autocorrelation function of the useful signal is acquired, and the Fourier transform is performed on the basis of the autocorrelation function to obtain the power spectrum of the useful signal. The corresponding skewness and kurtosis are acquired on the basis of the obtained power spectrum. The process can be defined as a third-level evaluation process that can evaluate the indicator related to the power spectrum. It can be understood that the evaluation process of the first-level and the second-level is to evaluate the signal from the perspective of an overall indicator, when discontinuous points and spike pulses occur in a local small region in the signal, these sudden changes cause the power spectrum coefficients to be distributed on the whole frequency axis, and a good sparse representation cannot be obtained. As shown in FIG. 6 and FIG. 7, in this case, whether an abnormality caused by a sudden change region occurs in a signal can be well distinguished through a power spectrum indicator.

In a specific embodiment, an autocorrelation function for performing a one-sided normalization on the useful signal $X_s[n]$, a specific function $R[k]$ of the autocorrelation function is expressed as follows:

$$R[k] = \frac{\sum_{n=0}^{N-1-k} x_s[n] x_s[n+k]}{\sum_{n=0}^{N-1} (x_s[n])^2}, k = 0, 1, \ldots, N-1;$$

It can be understood that, since N is the number of points of the useful signal, the length of the autocorrelation function for performing one-sided normalization on the signal is also 1000 points. In order to distinguish an original signal x[n], the autocorrelation function is referred to as R[k], where k is an index value of the autocorrelation function, the value range of k is 0 to N−1, n represents an index value of the useful signal, and the value range of n is also 0 to N−1.

It can be seen from the Wiener-Khinchin theorem that Fourier transform of the autocorrelation function corresponds to a power spectrum of the signal. The power spectrum $P_{xx}(f)$ of the useful signal obtained by performing Fourier transform on the autocorrelation function R[k] meets the following expression:

$$P_{xx}(f) = \sum_{k=0}^{N-1} R[k] e^{-j2\pi kf}, f = 0, 1, \ldots, N-1;$$

the kurtosis $P_{SK}$ and the skewness $P_{KT}$ of the power spectrum are respectively as follows:

$$P_{SK} = \frac{1}{N} \sum_{f=0}^{N-1} \left[ \left( \frac{P_{xx}(f) - \mu}{\sigma} \right)^3 \right];$$

$$P_{KT} = \frac{1}{N} \sum_{f=0}^{N-1} \left[ \left( \frac{P_{xx}(f) - \mu}{\sigma} \right)^4 \right];$$

where μ is a mean value of $P_{xx}(f)$, and σ is a variance of $P_{xx}(f)$.

The skewness and the kurtosis of the power spectrum are determined at the same time. When both the skewness and the kurtosis meet the corresponding threshold requirement, that is, when both the skewness and the kurtosis are greater than the corresponding second threshold value requirement, the signal of the power spectrum is determined to be normal, and the subsequent action of the step S6 can continue to be executed. When any one of the skewness and the kurtosis of the power spectrum does not meet the corresponding second threshold value, it can be determined that the original PPG signal has a sudden change region, and in this case, the subsequent determining action is executed directly. That is, the original PPG signal can be directly determined to be a third-grade signal, and the quality evaluation process of the original PPG signal can be ended.

In an embodiment, in the step S5, a second threshold value corresponding to the skewness of the power spectrum is larger than or equal to 12, and a second threshold value corresponding to the kurtosis of the power spectrum is larger than or equal to 150. This is, the second threshold value corresponding to the skewness of the power spectrum and the second threshold value corresponding to the kurtosis of the power spectrum can be set respectively.

S6: Acquire an average peak period of the autocorrelation function, and determine whether the average peak period is within a second preset range, when the average peak period is within the second preset range, executing step S7, and otherwise, executing step S11. Specifically, because of the correlation between the signal calculated by the autocorrelation function and the time delay thereof, when the signal has a periodic component, the autocorrelation function has a maximum value at an integer multiple of the period. Therefore, the periodicity of the autocorrelation function can be checked by detecting the peak value of the autocorrelation function. That is, the average peak period of the autocorrelation function is determined. When the average peak period is within the second preset range, it is determined that the original PPG signal is within the normal range of a sampled signal such as a heart rate signal, and the action of the step S7 can be continued. When the average peak period of the autocorrelation function is not within the second preset range, it is determined that the original PPG signal is not within the normal range of the heart rate, in this case, the subsequent determining action can be executed directly, that is, the original PPG signal can be directly determined to be the third-grade signal, and the quality evaluation process of the original PPG signal is ended.

In an embodiment, the second preset range is greater than 0.3 s and less than 2 s. That is, in a specific embodiment, it can be set that when the average peak period is greater than 0.3 s and less than 2 s, it is determined that the average peak period is within the second preset range.

S7: acquiring a maximum peak value and a standard deviation of a peak period of the autocorrelation function, and determining whether the maximum peak value is larger than a third threshold value or the standard deviation of the peak period is smaller than a fourth threshold value, when the maximum peak value is larger than the third threshold value or the standard deviation of the peak period is smaller than the fourth threshold value, executing step S8, and otherwise, executing step S11. Specifically, when the average peak period of the autocorrelation function meets the requirement, that is, when it is determined that the original PPG signal is within the normal range of a detection signal, the maximum peak value and the standard deviation of the peak period of the autocorrelation function are determined, that is, the periodicity of the original PPG signal is determined. When it is determined that the original PPG signal is periodic, the action of the step S8 can be continued. When it is determined that the original PPG signal is not periodic, the subsequent determining action can be executed directly, that is, the original PPG signal can be directly determined to be the third-grade signal, and the quality evaluation process of the original PPG signal is ended. The specific determining process is that when the maximum peak value of the autocorrelation function is larger than the third threshold value and the standard deviation of the peak period is smaller than the fourth threshold value at the same time, it is determined that the original PPG signal is not periodic, and otherwise, it can be determined that the original PPG signal is periodic.

In an embodiment, the third threshold value is larger than or equal to 0.6, and the fourth threshold value is smaller than or equal to 5. Specifically, it can be determined that the original PPG signal is periodic when the maximum peak value of the autocorrelation function is larger than 0.6, or it can be determined that the original PPG signal is periodic when the standard deviation of the peak period of the autocorrelation function is smaller than 5.

S8: Acquire a standard deviation of a peak-to-peak difference value of the autocorrelation function, and determine whether the standard deviation of the peak-to-peak difference value is smaller than a fifth threshold value, when the standard deviation of the peak-to-peak difference value is smaller than the fifth threshold value, execute step S9, and otherwise, execute step S10; S9: determine the original PPG signal to be a first-grade signal, and end; S10: determine the original PPG signal to be a second-grade signal, where quality of the second-grade signal is lower than that of the first-grade signal, and end; and S11: determine the original PPG signal to be a third-grade signal, where quality of the third-grade signal is lower than that of the second-grade signal, and end. Specifically, when it is determined, based on the maximum peak value and the standard deviation of the peak period of the autocorrelation function, that the original PPG signal is periodic within the normal range of the detection signal, the standard deviation of the peak difference of the autocorrelation function is determined. It is determined whether the form of a signal of each period of the original PPG signal is similar on the basis of the standard deviation of the peak-to-peak difference value. When the standard deviation of the peak-to-peak difference value of the autocorrelation function is smaller than a fifth threshold value, it can be determined that the form of the signal of each period is similar. In this case, it can be determined that the original PPG signal to be the first-grade signal, and otherwise, it is determined that the original PPG signal is the second-grade signal. The quality of the first-grade signal is better than that of the second-grade signal, and the quality of the second-grade signal is better than that of the third-grade signal.

Optionally, the PPG signal quality evaluation method of the present invention further includes: performing peak detection on the autocorrelation function by using a valley detection algorithm based on the second derivative to obtain a plurality of peak coordinates; and respectively acquiring an average peak period, a maximum peak value, a standard deviation of the peak period and a standard deviation of a peak-to-peak difference value of the autocorrelation function on the basis of the plurality of peak coordinates. Specifically, firstly, the peak detection can be performed on the autocorrelation function by using the valley detection algorithm based on the second derivative, to obtain w peak coordinates:

$$[(x_1^{peak}, y_1^{peak}), (x_2^{peak}, y_2^{peak}), \ldots, (x_w^{peak}, y_w^{peak})],$$

then the maximum peak value $R_{max}^{peak}$ of the autocorrelation function is:

$$R_{max}^{peak} = \max\left(y_1^{peak}, y_2^{peak}, \ldots, y_w^{peak}\right),$$

the adjacent peak-to-peak interval $R_i^{inter}$ is:

$$R_i^{inter} = x_{i+1}^{peak} - x_i^{peak},$$

then the average peak period $R_{period}$ of the autocorrelation function is:

$$R_{period} = \frac{1}{w}\sum_{i=1}^{w-1} R_i^{inter},$$

then the standard deviation of the peak period $R_{std}^{period}$ of the autocorrelation function is:

$$R_{std}^{period} = \sqrt{\frac{1}{w}\sum_{i=1}^{w-1}\left(R_i^{inter} - R_{period}\right)^2}$$

the peak-to-peak difference value $R_i^{diff}$ is:

$$R_i^{diff} = y_{i+1}^{peak} - y_i^{peak},$$

the average peak-to-peak difference value $R_{avg}^{diff}$ is:

$$R_{avg}^{diff} = \frac{1}{w}\sum_{i=1}^{w-1} R_i^{diff},$$

and then the standard deviation of the peak-to-peak difference value $R_{std}^{diff}$ of the autocorrelation function is:

$$R_{std}^{diff} = \sqrt{\frac{1}{w}\sum_{i=1}^{w-1}\left(R_i^{diff} - R_{avg}^{diff}\right)^2}.$$

Figure 8:
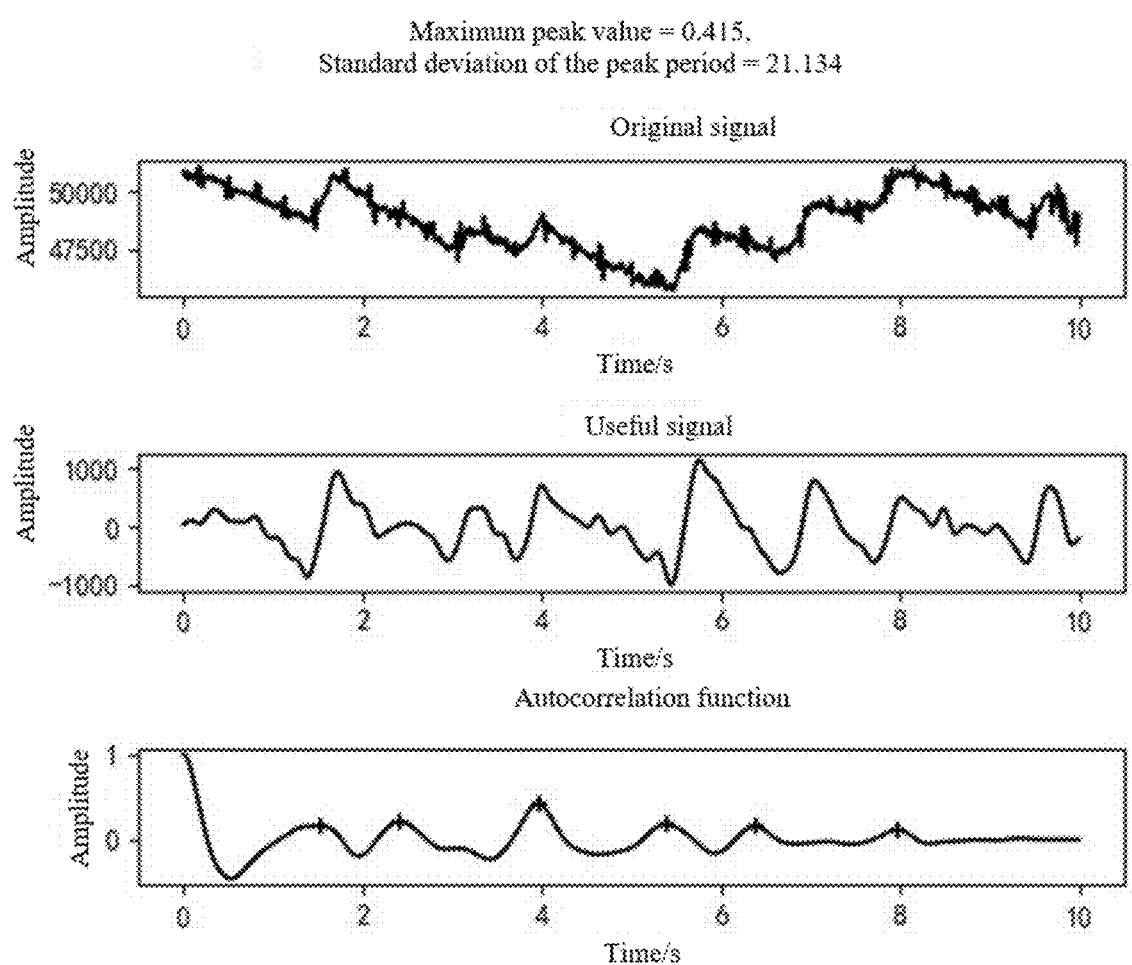
FIG. 8 is a schematic diagram of an autocorrelation function indicator of an original PPG signal according to an embodiment of the present invention.
Figure 9:
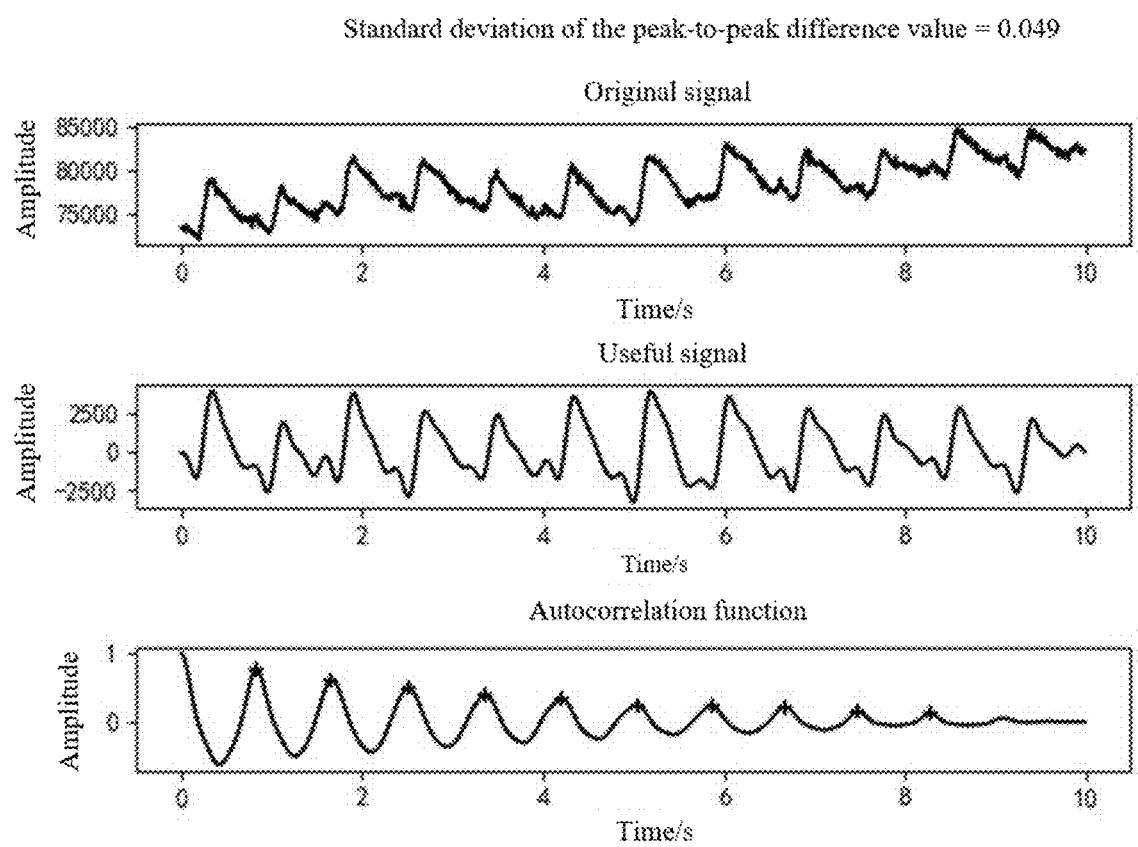
FIG. 9 is a schematic diagram of an autocorrelation function indicator of an original PPG signal according to another embodiment of the present invention.
Figure 10:
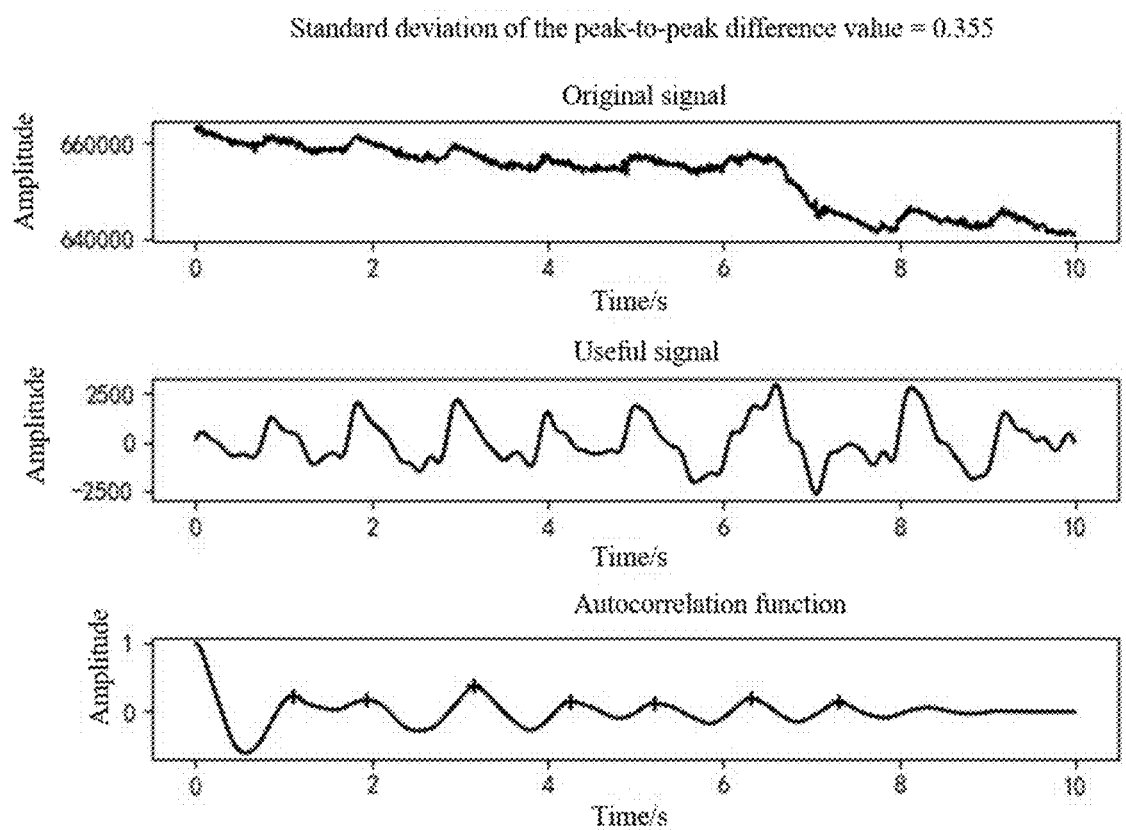
FIG. 10 is a schematic diagram of an autocorrelation function indicator of still another original PPG signal according to an embodiment of the present invention.

The process of determining an indicator related to the autocorrelation function can be defined as a fourth-level evaluation. Compared with directly performing periodic inspection on the useful signal, the calculation of the autocorrelation function can eliminate the influence of additive noise on the periodicity of an inspection signal. The average peak period of the autocorrelation function corresponds to the period of the original PPG signal. The average peak period should be between 0.3 s and 2 s according to the normal heart rate of 30-200 times per minute, and a signal exceeding the normal heart rate range is evaluated as a poor signal (as shown in FIG. 8). When the maximum peak value of the autocorrelation function is larger than 0.6 or the standard deviation of the peak period of the autocorrelation function is smaller than 5, it can be determined that the signal is periodic, and the accuracy is higher by using a periodic signal to calculate the heart rate and other physiological indicators. In this case, when the consistency and similarity of the form of the PPG signals in adjacent periods are higher, the autocorrelation function should be a gradually attenuated sine wave signal, while the form of the waveform of individual periodic signals may be affected by noise in a pass band, and the form of waveforms of the PPG signals in adjacent periods are different. In this case, the peak value of the autocorrelation function fluctuates, so that the fluctuation condition of the peak value of the autocorrelation function can be determined by calculating the standard deviation of the peak-to-peak difference value of the autocorrelation function. When the standard deviation of the peak-to-peak difference value of the autocorrelation function is smaller than 0.07, the signal is evaluated as a good signal (as shown in FIG. 9), otherwise, the signal is evaluated as a medium signal (as shown in FIG. 10).

According to the level relationship of signal quality evaluation in the process, if the quantitative indicator of the previous layer cannot meet the requirement, the next level of determination does not need to be performed, so that the probability of false detection can be effectively reduced, and the accuracy of the quality evaluation algorithm is improved.

In addition, a PPG signal processing method of the present invention includes: acquiring a quality evaluation result of an original PPG signal through the PPG signal quality evaluation method according to any one of the above; and when the original PPG signal is a third-grade signal, eliminating the original PPG signal; when the original PPG signal is a second-grade signal, using the original PPG signal to calculate partial preset physiological indicators; and when the original PPG signal is a first-grade signal, using the original PPG signal to calculate all physiological indicators related to the PPG signal. That is, in the PPG signal processing process, different operations are performed on the obtained PPG signals of different grades on the basis of the above PPG signal quality evaluation method. The third-grade signal is directly eliminated, and the second-grade signal is used as a calculation process of partial indicators such as heart rate, where the partial indicators are preset partial indicators. The first-grade signal can be normally used, that is, the first-grade signal can be used to calculate all physiological indicators such as heart rate and blood pressure, where the all physiological indicators are physiological indicators related to PPG.

Figure 11:
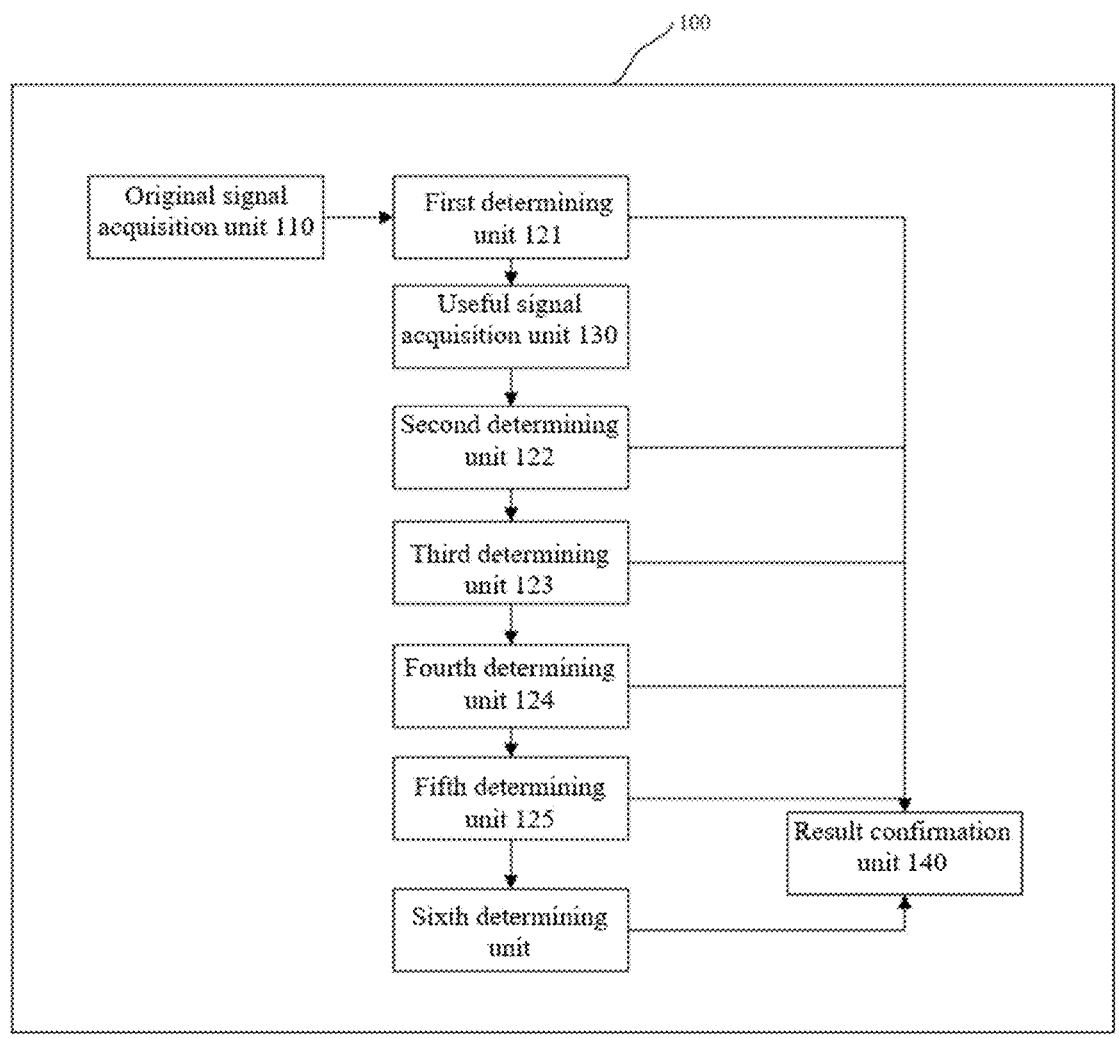
FIG. 11 is a logic block diagram of a PPG signal quality evaluation apparatus according to an embodiment of the present invention.

In addition, as shown in FIG. 11, a PPG signal quality evaluation apparatus 100 of the present invention includes:
an original signal acquisition unit 110, configured to acquire an original PPG signal in a preset duration, where the PPG signal is a photoplethysmography signal;
a first determining unit 121, configured to preprocess the original PPG signal to obtain a plurality of waveform segments in preset lengths, acquire average amplitude difference of the plurality of waveform segments, and determine whether the average amplitude difference is within a first preset range, when the average amplitude difference is within the first preset range, output a positive result, and otherwise, output a negative result;
a useful signal acquisition unit 130, configured to perform high-pass filtering and low-pass filtering on the original PPG signal respectively, and acquire a useful signal of the original PPG signal on the basis of the results of the high-pass filtering and low-pass filtering;

a second determining unit 122, configured to acquire a high-frequency signal-to-noise ratio of the original PPG signal on the basis of the useful signal and the result of the high-pass filtering, acquire a low-frequency signal-to-noise ratio of the original PPG signal on the basis of the useful signal and the result of the low-pass filtering, and determine whether the high-frequency signal-to-noise ratio and the low-frequency signal-to-noise ratio are respectively greater than corresponding first threshold values, when the high-frequency signal-to-noise ratio and the low-frequency signal-to-noise ratio are respectively greater than corresponding first threshold values, output a positive result, and otherwise, output a negative result;

a third determining unit 123, configured to acquire an autocorrelation function of the useful signal, perform Fourier transform on the autocorrelation function to obtain a power spectrum of the useful signal, acquire kurtosis and skewness of the power spectrum respectively, and determine whether the kurtosis and the skewness of the power spectrum are respectively greater than corresponding second threshold values, when the kurtosis and the skewness of the power spectrum are respectively greater than corresponding second threshold values, output a positive result, and otherwise, output a negative result;

a fourth determining unit 124, configured to acquire an average peak period of the autocorrelation function, and determine whether the average peak period is within a second preset range, when the average peak period is within the second preset range, output a positive result, and otherwise, output a negative result;

a fifth determining unit 125, configured to acquire a maximum peak value and a standard deviation of a peak period of the autocorrelation function, and determine whether the maximum peak value is larger than a third threshold value or the standard deviation of the peak period is smaller than a fourth threshold value, when the maximum peak value is larger than the third threshold value or the standard deviation of the peak period is smaller than the fourth threshold value, output a positive result, and otherwise, output a negative result;

a sixth determining unit 126, configured to acquire a standard deviation of a peak-to-peak difference value of the autocorrelation function, and determine whether the standard deviation of the peak-to-peak difference value is smaller than a fifth threshold value, when the standard deviation of the peak-to-peak difference value is smaller than the fifth threshold value, output a positive result, and otherwise, output a negative result; and a result confirmation unit 140, configured to determine that the original PPG signal is a third-grade signal when any one of the first determining unit 121, the second determining unit 122, the third determining unit 123, the fourth determining unit 124 and the fifth determining unit 125 outputs a negative result, determine that the original PPG signal is a second-grade signal when the sixth determining unit 126 outputs a negative result, and determine that the original PPG signal is a first-grade signal when the sixth determining unit 126 outputs a positive result, where quality of the third-grade signal is lower than that of the second-grade signal, and quality of the second-grade signal is lower than that of the first-grade signal. Specifically, a specific cooperative operation process between units of the PPG signal quality evaluation apparatus herein may refer to the foregoing PPG signal quality evaluation method, and details are not described herein again.

Figure 12:
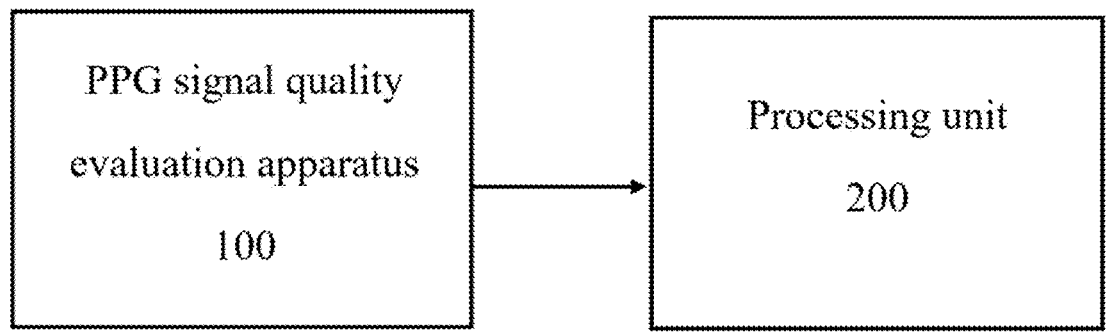
FIG. 12 is a logic block diagram of a PPG signal quality processing system according to an embodiment of the present invention.

In addition, as shown in FIG. 12, a PPG signal processing system of the present invention includes a PPG signal quality evaluation apparatus 100, and a processing unit 200. The processing unit is configured to acquire a quality evaluation result of an original PPG signal; and when the original PPG signal is a third-grade signal, eliminating the original PPG signal; when the original PPG signal is a second-grade signal, using the original PPG signal to calculate partial preset physiological indicators; and when the original PPG signal is a first-grade signal, using the original PPG signal to calculate all physiological indicators related to the PPG signal. That is, in the processing process of the PPG signal processing system, PPG signals of different grades are obtained through the above PPG signal quality evaluation apparatus, and different operations are performed on the obtained PPG signals of different grades through the processing unit. The third-grade signal is directly eliminated, and the second-grade signal is used as a calculation process of partial indicators such as heart rate, where the partial indicators are preset partial indicators. The first-grade signal can be normally used, that is, the first-grade signal can be used to calculate all physiological indicators such as heart rate and blood pressure, where the all physiological indicators are physiological indicators related to PPG.

It can be understood that the above embodiments merely illustrate the preferred embodiments of the present invention, and the description thereof is relatively specific and detailed, but it should not be construed as a limitation on the patent scope of the present invention. It should be noted that a person of ordinary skill in the art can freely combine the technical features and make several variants and improvements without departing from the concept of the present invention, which all fall within the protection scope of the present invention. Therefore, any equivalent transformation and modification made in accordance with the scope of the claims of the present invention shall fall within the scope of the claims of the present invention.

What is claimed is:

1. A Photoplethysmograph (PPG) signal quality evaluation method, comprising:

S1: acquiring an original PPG signal in a preset duration, wherein the PPG signal is a photoplethysmography signal;

S2: preprocessing the original PPG signal to obtain a plurality of waveform segments in preset lengths, acquiring average amplitude difference of the plurality of waveform segments, and determining the average amplitude difference is within a first preset range;

S3: performing high-pass filtering and low-pass filtering on the original PPG signal respectively, and acquiring a useful signal of the original PPG signal on the basis of the results of the high-pass filtering and low-pass filtering;

S4: acquiring a high-frequency signal-to-noise ratio of the original PPG signal on the basis of the useful signal and the result of the high-pass filtering, acquiring a low-frequency signal-to-noise ratio of the original PPG signal on the basis of the useful signal and the result of the low-pass filtering, and determining the high-frequency signal-to-noise ratio and the low-frequency signal-to-noise ratio are respectively greater than corresponding first threshold values, S5: acquiring an autocorrelation function of the useful signal, performing Fourier transform on the autocorrelation function to obtain a power spectrum of the useful signal, acquiring kurtosis and skewness of the power spectrum respectively, and determining whether the kurtosis and the skewness of the power spectrum are respectively greater than corresponding second threshold values;

S6: acquiring an average peak period of the autocorrelation function, and determining the average peak period is within a second preset range;

S7: acquiring a maximum peak value and a standard deviation of a peak period of the autocorrelation function, and determining the maximum peak value is larger than a third threshold value or the standard deviation of the peak period is smaller than a fourth threshold value;

S8: acquiring a standard deviation of a peak-to-peak difference value of the autocorrelation function, and determining the standard deviation of the peak-to-peak difference value is smaller than a fifth threshold value;

S9: determining the original PPG signal grade based on the above steps S1-S8, and ending.

2. The PPG signal quality evaluation method according to claim 1, wherein in the step S1, the preset duration is greater than or equal to 5 s and less than or equal to 15 s.

3. The PPG signal quality evaluation method according to claim 1, wherein in the step S2,
the preprocessing the original PPG signal to obtain a plurality of waveform segments in preset lengths comprises:
performing median filtering on the original PPG signal, and sequentially performing non-interval interception on a filtered signal using a sliding window of the preset length to obtain the plurality of waveform segments, wherein the waveform segments do not overlap; and/or,
the acquiring average amplitude difference of the plurality of waveform segments comprises:
acquiring amplitude difference of each waveform segment, and acquiring an average value of amplitude difference of all the waveform segments as the average amplitude difference.

4. The PPG signal quality evaluation method according to claim 1, wherein
the first preset range is greater than or equal to 150 and less than or equal to 90000; and/or,
the preset length is 1 s.

5. The PPG signal quality evaluation method according to claim 1, wherein in the step 3, the performing high-pass filtering and low-pass filtering on the original PPG signal respectively, and acquiring a useful signal of the original PPG signal on the basis of the results of the high-pass filtering and low-pass filtering comprises:

S31: performing high-pass filtering on the original PPG signal through a Butterworth high-pass filter with a cutoff frequency as a first frequency to obtain a high-frequency noise signal;

S32: performing low-pass filtering on the original PPG signal through a Butterworth high-pass filter with a cutoff frequency as a second frequency to obtain a low-frequency noise signal; and S33: eliminating the high-frequency noise signal and the low-frequency noise signal from the original PPG signal respectively, and using a residual signal as the useful signal.

6. The PPG signal quality evaluation method according to claim 5, wherein in the step S4,
the acquiring a high-frequency signal-to-noise ratio of the original PPG signal on the basis of the useful signal and the result of the high-pass filtering comprises: acquiring a ratio of the high-frequency noise signal to the useful signal as the high-frequency signal-to-noise ratio; and
the acquiring a low-frequency signal-to-noise ratio of the original PPG signal on the basis of the useful signal and the result of the low-pass filtering comprises: acquiring a ratio of the low-frequency noise signal to the useful signal as the low-frequency signal-to-noise ratio.

7. The PPG signal quality evaluation method according to claim 1, wherein in the step 4, a first threshold value corresponding to the high-frequency signal-to-noise ratio is larger than or equal to 6 dB, and the first threshold value corresponding to the low-frequency signal-to-noise ratio is larger than or equal to −15 dB; and/or,
in the step S5, a second threshold value corresponding to the skewness of the power spectrum is larger than or equal to 12, and a second threshold value corresponding to the kurtosis of the power spectrum is larger than or equal to 150.

8. The PPG signal quality evaluation method according to claim 1, wherein in the step 5, the acquiring an autocorrelation function of the useful signal comprises: an autocorrelation function for performing a one-sided normalization on the useful signal, wherein the autocorrelation function meets the following formula:

$$R[k] = \frac{\sum_{n=0}^{N-1-k} x_s[n]x_s[n+k]}{\sum_{n=0}^{N-1}(x_s[n])^2}, k = 0, 1, \ldots, N-1$$

wherein R[k] is the autocorrelation function, k is an index value of the autocorrelation tion, $x_s[n]$ is the useful signal, n is an index value of the useful signal, and N is the number of points of the useful signal.

9. The PPG signal quality evaluation method according to claim 1, wherein the method further comprises:
performing peak detection on the autocorrelation function by using a valley detection algorithm based on the second derivative to obtain a plurality of peak coordinates; and
respectively acquiring an average peak period, a maximum peak value, a standard deviation of the peak period and a standard deviation of a peak-to-peak difference value of the autocorrelation function on the basis of the plurality of peak coordinates.

10. The PPG signal quality evaluation method according to claim 1, wherein the method comprises one or more of the following parameter settings:
the second preset range is greater than 0.3 s and less than 2 s;
the third threshold value is larger than or equal to 0.6;
the fourth threshold value is smaller than or equal to 5; and
the fifth threshold value is smaller than or equal to 0.07.

11. The PPG signal quality evaluation method according to claim 1,
S10: determining the original PPG signal to be a first-grade signal, and ending;
S11: determining the original PPG signal to be a second-grade signal, wherein quality of the second-grade signal is lower than that of the first-grade signal, and ending; and
S12: determining the original PPG signal to be a third-grade signal, wherein quality of the third-grade signal is lower than that of the second-grade signal, and ending.

12. The PPG signal quality evaluation method according to claim 11 wherein, when the original PPG signal is a third-grade signal, eliminating the original PPG signal;

when the original PPG signal is a second-grade signal, using the original PPG signal to calculate partial preset physiological indicators; and when the original PPG signal is a first-grade signal, using the original PPG signal to calculate all physiological indicators related to the PPG signal.

\* \* \* \* \*